United States Patent
Maier et al.

(10) Patent No.: US 11,224,758 B2
(45) Date of Patent: Jan. 18, 2022

(54) IRRADIATION DEVICE AND METHOD FOR IRRADIATING A RADIATION ABSORBING MEDIUM, HEARING AID DEVICE AND LASER SURGERY DEVICE, IN PARTICULAR FOR LASER EAR SURGERY, WITH SUCH AN IRRADIATION DEVICE

(71) Applicant: MEDIZINISCHE HOCHSCHULE HANNOVER, Hannover (DE)

(72) Inventors: Hannes Maier, Hannover (DE); Waldo Nogueira-Vazquez, Hannover (DE); Andreas Buechner, Isenhagen (DE); Thomas Lenarz, Hannover (DE); Andrej Kral, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 0 days.

(21) Appl. No.: 16/625,913

(22) PCT Filed: Jun. 27, 2018

(86) PCT No.: PCT/EP2018/067243
§ 371 (c)(1),
(2) Date: Dec. 23, 2019

(87) PCT Pub. No.: WO2019/002365
PCT Pub. Date: Jan. 3, 2019

(65) Prior Publication Data
US 2020/0171320 A1    Jun. 4, 2020

(30) Foreign Application Priority Data
Jun. 28, 2017 (EP) .................................. 17178294

(51) Int. Cl.
*A61N 5/06* (2006.01)
*H04R 25/00* (2006.01)
(Continued)

(52) U.S. Cl.
CPC .......... *A61N 5/0603* (2013.01); *H04R 25/603* (2019.05); *A61B 2017/00159* (2013.01);
(Continued)

(58) Field of Classification Search
CPC .............. A61F 11/00; A61N 2005/063; A61N 2005/0605; A61N 5/0603; A61B 18/26; A61B 2018/00327; A61B 2017/00159
See application file for complete search history.

(56) References Cited

U.S. PATENT DOCUMENTS

| | | | |
|---|---|---|---|
| 2012/0089132 A1 | 4/2012 | Dick et al. | |
| 2014/0243805 A1* | 8/2014 | Dick | A61N 5/06 606/11 |

(Continued)

FOREIGN PATENT DOCUMENTS

WO    WO 2010/086452    8/2010

OTHER PUBLICATIONS

International Search Report and Written Opinion for International (PCT) Patent Application No. PCT/EP2018/067243, dated Sep. 14, 2018, 11 pages.

*Primary Examiner* — Carl H Layno
*Assistant Examiner* — Aya Ziad Bakkar
(74) *Attorney, Agent, or Firm* — Sheridan Ross P.C.

(57) ABSTRACT

The invention relates to an irradiation device and a corresponding method for irradiating a radiation absorbing medium, as well as a hearing aid device and a laser surgery device comprising such an irradiation device. A radiation source is configured to generate one or more pulses of electromagnetic radiation and to irradiate the medium with the one or more pulses of electromagnetic radiation. A control unit is configured to control the radiation source such that the time course of the power or intensity of at least one pulse of the one or more pulses of electromagnetic radiation (Continued)

exhibits a rising slope and/or a falling slope, wherein the rising slope and/or falling slope has a maximum gradient which is smaller than a predetermined gradient value, whereby a generation of optoacoustic waves in the medium in response to the rising slope or falling slope, respectively, is avoided or significantly reduced.

13 Claims, 3 Drawing Sheets (51) Int. Cl.
*A61B 18/00* (2006.01)
*A61B 17/00* (2006.01)
*A61N 5/067* (2006.01)

(52) U.S. Cl.
CPC ............... *A61B 2018/00327* (2013.01); *A61N 2005/063* (2013.01); *A61N 2005/0605* (2013.01); *A61N 2005/067* (2013.01)

(56) References Cited

U.S. PATENT DOCUMENTS

2015/0374988 A1* 12/2015 Laudanski ........... A61N 1/0529
                                              607/57
2017/0134865 A1*  5/2017 Goldstein ............ A61N 5/0613

* cited by examiner

IRRADIATION DEVICE AND METHOD FOR IRRADIATING A RADIATION ABSORBING MEDIUM, HEARING AID DEVICE AND LASER SURGERY DEVICE, IN PARTICULAR FOR LASER EAR SURGERY, WITH SUCH AN IRRADIATION DEVICE

CROSS REFERENCE TO RELATED APPLICATIONS

This application is a national stage application under 35 U.S.C. 371 and claims the benefit of PCT Application No. PCT/EP2018/067243 having an international filing date of 27 Jun. 2018, which designated the United States, which PCT application claimed the benefit of European Patent Application No. 17178294.9 filed 28 Jun. 2017, the disclosures of each of which are incorporated herein by reference in their entireties.

TECHNICAL FIELD

The present invention relates to an irradiation device and method for irradiating a radiation absorbing medium, a hearing aid device and a laser surgery device, in particular for laser ear surgery, with such an irradiation device.

BACKGROUND OF THE INVENTION

Irradiating a radiation absorbing medium, for example biological tissue, with transient electromagnetic energy, for example light, causes a temporary local expansion or contraction of the medium resulting in a generation of acoustic waves. This effect is known as the photoacoustic or optoacoustic effect.

The optoacoustic effect is of particular interest in the treatment of sensorineural hearing loss, whereby optoacoustic pressure waves are generated which act on the basilar membrane of the cochlea in the inner ear resulting in an action potential response of spiral ganglion neurons (SGNs).

On the other hand, during laser surgical treatments of the ear or regions close to the ear occurring optoacoustic waves may cause or promote a hearing damage.

SUMMARY OF THE INVENTION

It is an object of the invention to provide an irradiation device and method for irradiating a radiation absorbing medium, a hearing aid device and a laser surgery device, in particular for laser ear surgery, which are improved regarding sound generation.

The object is achieved by the irradiation device, the method, the hearing aid device and the laser surgery device according to the independent claims.

An irradiation device according to the invention comprises a radiation source configured to generate one or more pulses of electromagnetic radiation and to irradiate the medium with the one or more pulses of electromagnetic radiation, and a control unit configured to control the radiation source such that the time course of the power or intensity of at least one pulse of the one or more pulses of electromagnetic radiation exhibits a rising slope and/or a falling slope, wherein the rising slope and/or falling slope has a maximum gradient which is smaller than a predetermined gradient value, whereby a generation of optoacoustic waves in the medium in response to the rising slope or falling slope, respectively, is avoided or significantly reduced.

A hearing aid device according to the invention comprises the irradiation device according to the invention, wherein the radiation source, in particular a laser diode and a light guide coupled to the laser diode, or a part of the radiation source, in particular a part of the light guide, is dimensioned and/or designed for being placed in the ear, in particular in the middle or inner ear, and designed for irradiating a component of the ear or a radiation absorbing medium located in proximity of or adjacently to a component of the ear with the at least one pulse of electromagnetic radiation.

A laser surgery device, in particular for laser ear surgery, according to the invention comprises the irradiation device according to the invention, wherein the radiation source comprises a laser source and is dimensioned and/or designed for irradiating an organ of a human, in particular a component of the ear, with the at least one pulse of electromagnetic radiation.

A method for irradiating a radiation absorbing medium according to the invention comprises generating one or more pulses of electromagnetic radiation and irradiating the medium with the one or more pulses of electromagnetic radiation, wherein the time course of the power or intensity of at least one pulse of the one or more pulses of electromagnetic radiation exhibits a rising slope and/or a falling slope, the rising slope and/or falling slope having a maximum gradient which is smaller than a predetermined gradient value, whereby a generation of optoacoustic waves in the medium in response to the rising slope or falling slope, respectively, is avoided or significantly reduced.

In a method for controlling an irradiation device, which is configured to irradiate a radiation absorbing medium, according to another aspect of the invention the irradiation device is controlled to generate one or more pulses of electromagnetic radiation and irradiate the medium with the one or more pulses of electromagnetic radiation, wherein the time course of the power or intensity of at least one pulse of the one or more pulses of electromagnetic radiation exhibits a rising slope and/or a falling slope, the rising slope and/or falling slope having a maximum gradient which is smaller than a predetermined gradient value, whereby a generation of optoacoustic waves in the medium in response to the rising slope or falling slope, respectively, is avoided or significantly reduced.

The invention is based on the approach to provide an irradiation device, a hearing aid device or a laser surgery device with a radiation source or laser source, respectively, which is configured and/or controlled to irradiate a human organ, in particular a component of the middle or inner ear, or a radiation absorbing medium located close to the organ with pulses of electromagnetic radiation exhibiting a non-rectangular shape. Rather than generating rectangular pulses exhibiting both a steep rising edge and a steep falling edge, the radiation or laser source is configured and/or controlled to generate pulses, whose rising edge and/or falling edge is or are given by a rising slope and/or falling slope, respectively, having a finite and/or limited gradient. In particular, the rising and/or falling slope exhibits a maximum gradient, which is below a predetermined gradient or gradient value. The term "maximum gradient" preferably relates to the maximum absolute value of the gradient of the time course of power P or intensity I of a rising or falling slope:

$$\mathrm{abs}\left(\frac{\Delta P}{\Delta t}\right)_{max} \text{ or } \mathrm{abs}\left(\frac{\Delta I}{\Delta t}\right)_{max}.$$

For example, in case of a linearly rising or falling slope, the maximum gradient corresponds to the (only one) gradient of the straight rising or falling line, respectively. For example, in case of a curved rising or falling slope, e.g. an exponentially rising or falling slope, the maximum gradient corresponds to the gradient of the slope at a time point where the gradient is maximal, for example at or close to a time point, where the power or intensity of the pulse is maximal.

As a result, when irradiating the organ or medium with accordingly shaped pulses optoacoustic waves are generated only in response to a steep rising or falling edge, respectively, whereas a generation of optoacoustic waves in response to the continuously rising or falling slope, the gradient of which is limited, is avoided or significantly reduced.

For example, the radiation source of the hearing aid device is configured and/or controlled to generate pulses each of which exhibiting a steep rising edge and a falling slope having a limited gradient. As a result, in the irradiated component of the ear or the radiation absorbing medium located in proximity of or adjacently to a component of the ear sound pulses are only generated in response to the steep rising edge, also referred to as condensation sound pressure pulses, whereas in response to the subsequent falling slope no or only a negligible sound pressure pulse is generated. Accordingly, in case of pulses exhibiting a rising slope having a limited gradient and a steep falling edge no or only a negligible sound pressure pulse is generated in response to the rising slope, whereas in response to the subsequent and steep falling edge a sound pressure pulse, also referred to as rarefaction sound pressure pulses, is generated. In this way it can be ensured that, in response to an irradiation of the component or medium with accordingly shaped pulses, optoacoustic sound pressure pulses are generated which contain either condensation or rarefaction sound pressure pulses only, rather than both condensation and rarefaction sound pressure pulses as with an irradiation with rectangular pulses. As a result, in contrast to an irradiation of the component or medium with rectangular pulses exhibiting both steep rising and steep falling edges, a series of condensation sound pressure pulses can be generated which is not affected by rarefaction sound pressure pulses and vice versa. As a result, the hearing aid device allows for a generation of optoacoustic sound in the component or medium with improved sound quality by series of selective condensation or rarefaction pulses.

According to another example, the laser source of the laser surgery device is configured and/or controlled to generate pulses each of which exhibiting both a rising slope and a falling slope having a limited gradient. As a result, in the irradiated organ, in particular a component of the ear, no or only negligible sound pressure pulses are generated. Thus, the laser surgery device allows for an application of laser energy to the organ for surgical and/or treatment purposes without generating optoacoustic sound waves at the same time. This is particularly advantageous in, but not limited to, the field of laser ear surgery (otosurgery) where optoacoustically generated sound waves, which may lead to sensorineural hearing loss or impairment at commonly used laser power levels, can be suppressed or at least significantly reduced.

In summary, the invention provides an irradiation device for irradiating a radiation absorbing medium, a hearing aid device and a laser surgery device, in particular for laser ear surgery, with improved capabilities regarding optoacoustic sound generation.

Preferably, the radiation source is configured to generate a series of pulses of electromagnetic radiation and the control unit is configured to control the radiation source such that the time course of the power or intensity of at least one pulse or each pulse of the series of pulses exhibits a rising slope and/or falling slope the maximum gradient of which being smaller than the predetermined gradient value. In case that the time course of the power or intensity of pulses, in particular of each pulse, of the series exhibits either an accordingly rising or an accordingly falling slope, a series of either condensation or rarefaction, respectively, sound pressure pulses can be generated, which is of particular advantage for hearing aid applications of the irradiation device. In case that the time course of the power or intensity of pulses, in particular of each pulse, of the series exhibits both an accordingly rising and an accordingly falling slope, electromagnetic energy of the series of pulses can be deposited in the medium without generating sound pressure pulses, which is of particular advantage, e.g., in laser surgery applications of the irradiation device.

In a preferred embodiment of the invention, the rising slope and/or falling slope is a continuously or gradually rising slope or a continuously or gradually falling slope, respectively. Preferably, the term "continuously rising" and "continuously falling" relates to a successive or gradual increase or decrease, respectively, of the time course of the power or intensity of the electromagnetic radiation in the pulse. In particular, the continuously rising or falling slope does not contain a discontinuous increase or decrease of power or intensity. In this way, optoacoustic sound generation and/or suppression in the radiation absorbing medium or a component of the ear can be controlled in a particular reliable and simple way. In particular, the radiation absorbing medium, e.g. the tympanic membrane or other structures of the middle or inner ear, may be systematically stimulated in order to provide sound input with high fidelity and spatial resolution.

Preferably, the continuously or gradually rising slope or the continuously or gradually falling slope corresponds to a change in the deposition rate of electromagnetic energy of the electromagnetic radiation in the medium below a predetermined threshold, wherein said predetermined threshold lies below the onset of acoustic wave generation with significant amplitudes.

In another preferred embodiment, the falling slope is a linearly falling slope and/or the rising slope is a linearly rising slope. For example, the linearly falling slope or the linearly rising slope may be part of a sawtooth- and/or triangular-shaped pulse. For example, the gradient of the linearly falling slope or the linearly rising slope may be predetermined by adjusting the pulse duration at a constant maximum power or intensity of the pulse. In this way, the maximum gradient of the rising slope and/or falling slope can be kept below the predetermined gradient value in a particularly reliable and simple manner, which further improves the capabilities of controlling optoacoustic sound generation and/or suppression in the radiation absorbing medium or a component of the ear.

In yet another preferred embodiment, the falling slope is differentiable and/or the rising slope is differentiable. Preferably, the term "differentiable" is used in its mathematical meaning according to which the first time derivative of the falling or rising slope exists and has finite values at each time point. By this means, it is also ensured in a particularly reliable way to keep the maximum gradient of the rising slope or falling slope below the predetermined gradient.

According to a preferred embodiment of the invention, the maximum gradient of the rising slope or falling slope, respectively, corresponds to the maximum of the absolute value of the first time derivative of the falling slope or rising slope, respectively. In this way, optoacoustic sound generation and/or suppression in the radiation absorbing medium or a component of the ear can be controlled in a particular reliable and simple way both with respect to so-called condensation and rarefaction sound pressure waves.

According to another preferred embodiment of the invention, the predetermined gradient value is dependent on or is calculable or calculated by considering: a maximum power applied to the medium by irradiating the medium with the at least one pulse of electromagnetic radiation, a length characterizing a dimension of a heat heterogeneity in the medium and/or corresponding to a decay constant of the electromagnetic energy deposition in the medium, and the thermal diffusivity of the medium. In particular, the length corresponds to a spatial dimension of the electromagnetic radiation, e.g. a diameter of a laser beam, or an absorption length of the electromagnetic radiation in the medium, whichever is smaller.

Preferably, the control unit is configured to determine the predetermined gradient value by dividing the maximum power or the maximum intensity of the at least one pulse of electromagnetic radiation generated by the irradiation source by the thermal confinement time constant, which is given by the absorbing volume to which the characteristic length of heat heterogeneity, e.g. the dimension of the optically absorbing target, or the decay constant of the optical energy deposition and the thermal diffusivity of the medium contribute.

By means of any of the above embodiments, the predetermined gradient value can be determined easily and reliably so that optoacoustic sound generation and/or suppression in the radiation absorbing medium or a component of the ear can be controlled in a particular reliable way.

According to yet another embodiment, in particular of the hearing aid according to the invention, the control unit is configured to control the radiation source such that the time course of the power or intensity of the at least one pulse exhibits either a falling slope having a maximal gradient which is smaller than a predetermined gradient value and a rising edge, or a rising slope having a maximal gradient which is smaller than a predetermined gradient value and a falling edge. By this means, each pulse of electromagnetic radiation induces a single dominant optoacoustic wave in the component of the ear or the radiation absorbing medium in response to the rising edge or falling edge, respectively, whereas in response to the falling slope and rising slope, respectively, no optoacoustic wave or only a negligible optoacoustic wave is generated. In this way, a well-defined series of either condensation or rarefaction sound wave pulses is obtained.

In yet another preferred embodiment, the rising edge is a discontinuously rising edge and/or the falling edge is a discontinuously falling edge. For example, the time course of the power or intensity of the pulse of electromagnetic radiation in the region of the rising or falling edge, respectively, exhibits a rectangular or almost rectangular shape. By this means, the rising edge or the falling edge, respectively, of the at least one pulse of electromagnetic radiation induces a particularly strong optoacoustic response in the component of the ear or the radiation absorbing medium. Alternatively or additionally, the maximum power or maximum intensity of the at least one pulse of electromagnetic radiation generated by the radiation source may also be increased to enhance the strength of the optoacoustic response.

In another preferred embodiment, the maximum of the absolute value of the first time derivative of the rising edge and/or the maximum of the absolute value of the first time derivative of the falling edge is larger than the predetermined gradient value. Preferably, the maximum of the absolute value of first time derivative of the rising edge and/or the maximum absolute value of the first time derivative of the falling edge is larger than the maximum of the absolute value of the first time derivative of the falling slope or the maximum absolute value of the first time derivative of the rising slope, respectively, preferably by at least two times, in particular at least four times, particularly preferred at least ten times. By this means, it is ensured that the optoacoustic response induced by the rising edge and/or the falling edge in the component of the ear or the radiation absorbing medium is significantly higher than the optoacoustic response induced by the respective falling or rising slope so that it dominates the composition of the generated condensation or rarefaction, respectively, acoustic pulses.

In yet another preferred embodiment, the time course of the power or intensity of the at least one pulse exhibits a sawtooth shape. The generation of the saw-tooth-shaped pules of electromagnetic radiation is particularly easy. By this means, the difference in amplitude of the optoacoustic response induced by the rising or falling edge, on the one hand, and the falling or rising slope, on the other hand, can be maximized.

According to another preferred embodiment of the invention, the radiation source comprises a radiation guiding element, in particular an optical light guide, e.g. an optical fiber, having a proximal end, into which the at least one pulse of electromagnetic radiation is coupled, and a distal end and being configured to guide the at least one pulse of electromagnetic radiation from the proximal end to the distal end, wherein the distal end is dimensioned and/or designed for being placed in the ear, in particular in the middle or inner ear, and designed for emitting the at least one pulse of electromagnetic radiation to the component of the ear or to the radiation absorbing medium located in proximity of or adjacently to a component of the ear. Preferably, the radiation source comprises a laser source, e.g. a laser diode, configured to generate the pulsed electromagnetic radiation. In order to couple the radiation into the radiation guiding element, a coupling element, e.g. a fiber coupler, maybe arranged between the laser source and the proximal end of the radiation guiding element. Preferably, the radiation guiding element is flexible such that the laser source may be carried at any desired position at the body, in particular arranged behind the ear. By this means, radiation sources providing a predetermined power output and exhibiting certain spatial dimensions, which prevent them from being placed in the ear, may be used in conjunction with the hearing aid device.

According to a preferred embodiment of the laser surgery device according to the invention, the control unit is configured to control the radiation source such that the time course of the power or intensity of the at least one pulse exhibits both a rising slope having a maximal gradient which is smaller than a predetermined gradient value and a falling slope having a maximal gradient which is smaller than a predetermined gradient value. By this means, in the absence of both a rising edge and a falling edge in the time course of the power or intensity of the at least one pulse a stimulation of according condensation or rarefaction, respectively, sound pressure waves is avoided or at least significantly reduced. In particular, this embodiment allows for a deposition of electromagnetic energy in an object or an organ of a subject without perturbing the object or organ, respectively, by acoustic waves.

Further advantages, features and examples of the present invention will be apparent from the following description of following figures:

DETAILED DESCRIPTION

Figure 1:
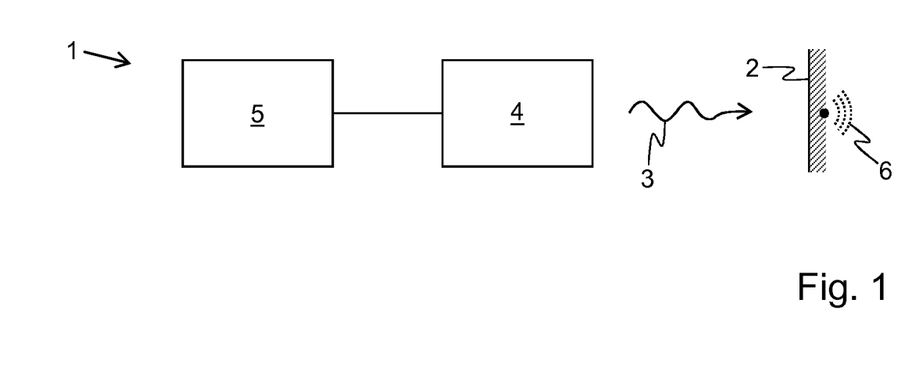
FIG. 1 shows an example of an irradiation device.

FIG. 1 shows an example of an irradiation device 1 for irradiating a radiation absorbing medium 2 with at least one pulse of electromagnetic radiation 3. The irradiation device 1 comprises a radiation source 4 and a control unit 5.

The radiation source 4, e.g. a laser source, in particular a laser diode, is configured to generate the electromagnetic radiation 3 which is emitted towards the radiation absorbing medium 2. Preferably, the radiation source 4 emits the electromagnetic radiation 3 at a wavelength, at which the radiation absorbing medium 2, e.g. tissue, exhibits a particularly strong absorption of the electromagnetic radiation 3. In particular, the wavelength is a wavelength at which an absorption coefficient of the radiation absorbing medium 2 exhibits a maximum. For example, the radiation source 4 is configured to generate electromagnetic radiation 3 at a wavelength in the near infrared spectrum, in particular between 0.7 µm and 2.2 µm, preferably between 1 µm and 1.9 µm, particularly preferable at approximately 1.55 µm and/or 1.85 µm. Alternatively or additionally, the radiation source 4 is configured to generate electromagnetic radiation 3 at a wavelength of approximately 0.6 µm. Preferably, the radiation source 4 is configured to generate electromagnetic radiation 3 at a variable frequency such that the frequency of the generated electromagnetic radiation 3 can be adapted to the absorption characteristics of the radiation absorbing medium 2, e.g. a component of an ear or an artificial implant in the ear.

Absorption of electromagnetic radiation 3 in the radiation absorbing medium 2 results in an optoacoustic response in the radiation absorbing medium 2. In particular, a change in the deposition rate of electromagnetic energy of the electromagnetic radiation 3 in the radiation absorbing medium 2 causes an expansion or contraction of a part of the radiation absorbing medium 2, e.g. cells of a tissue, such that acoustic waves 6 are generated, wherein the contracting or expanding part of the radiation absorbing medium 2 is preferably defined by one or more focal spots at which the electromagnetic radiation 3 is focused. A part of the radiation absorbing medium 2 may be, for example, a component of the ear, in particular the cochlear, or an artificial implant in the ear.

Preferably, the generation of acoustic waves 6 in the radiation absorbing medium 2 is adaptable to and/or controllable dependent on the particular application of the irradiation device 1, e.g. in a hearing aid device or in a laser surgery device.

To this end, the control unit 5 is configured to control the radiation source 4 to generate pulses of electromagnetic radiation 3, wherein the time course of the power or intensity of each pulse exhibits a rising slope and/or a falling slope, wherein said rising slope and/or falling slope has a limited gradient. In particular, the gradient of the slope or, in case that the slope exhibits more than one gradient value, the gradient values or the maximum gradient of the slope is smaller than a predetermined gradient value. For example, rather than generating a series of rectangular pulses, a series of pulses is generated each of which exhibiting a continuously rising and/or falling slope.

In other words, each pulse exhibits at least one non-abrupt, i.e. soft or moderate, rise or fall in the time course of its power or intensity, by which means the change in the deposition rate of electromagnetic energy in the radiation absorbing medium 2 is kept low enough to substantially prevent the generation of acoustic waves 6. A more detailed description to this end is given in conjunction with FIG. 3 below.

The irradiation device 1 shown in FIG. 1 may be configured as a laser surgery device, in particular for laser ear surgery, wherein the radiation source 4 comprises a laser source and is dimensioned and/or designed for irradiating an organ of a human, in particular a component of the ear, with the at least one pulse of electromagnetic radiation 3. Preferably, the control unit 5 is further configured to control the radiation source 4 such that the time course of the power or intensity of the at least one pulse exhibits both a rising slope having a maximum gradient which is smaller than a predetermined gradient value and a falling slope having a maximal gradient which is smaller than a predetermined gradient value.

Further, the irradiation device 1 shown in FIG. 1 may be used in and/or part of a hearing aid device as described in detail as follows.

Figure 2:
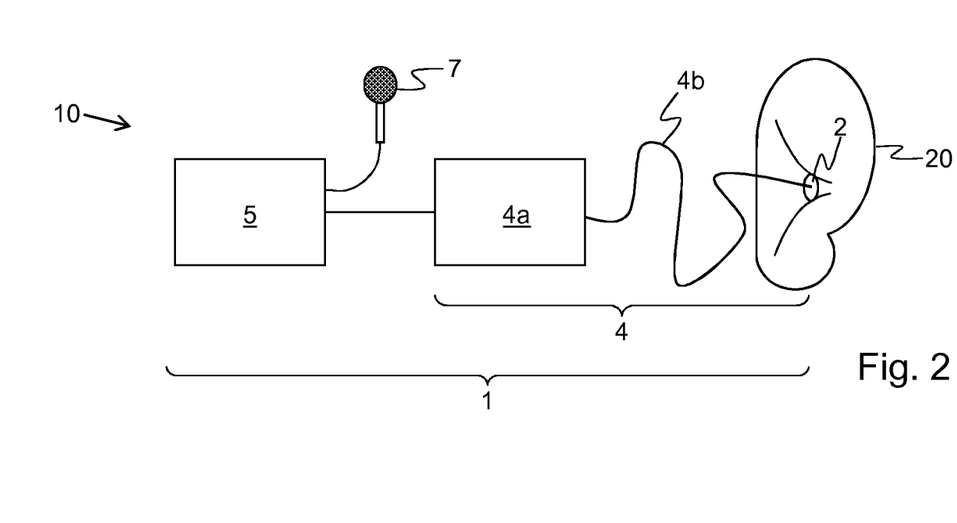
FIG. 2 shows an example of a hearing aid device.

FIG. 2 shows an example of a hearing aid device 10 comprising an irradiation device 1 for generating acoustic waves in a radiation absorbing medium 2. The radiation absorbing medium 2 can be, e.g., a natural component of a human ear 20, in particular a natural component of the middle or inner ear like the tympanum or basilar membrane, or a radiation absorbing medium inserted or implanted in the ear 20, for example implanted in the middle or inner ear, and being located in proximity to a natural component of the human ear 20, in particular a natural component of the middle or inner ear like the tympanum or basilar membrane. For sake of clarity, the ear 20 is represented in a very simplified manner, wherein the outer, middle and inner ear is represented only schematically. In the representation shown, the medium 2 is located in the middle and/or inner ear.

The irradiation device 1 comprises a control unit 5 configured to control a radiation source 4 to generate a series of pulses of electromagnetic radiation. In present example, the pulses are preferably shaped such that only one significant optoacoustic response per pulse is generated in the medium 2. That is, the optoacoustic response in the medium 2 contains a series of either compression or rarefaction sound pressure pulses.

Preferably, the control unit 5 may further comprise or be connected to a microphone 7 configured to detect sound by converting sound into electrical signals. The control unit 5 is preferably configured to control the irradiation source 4 to generate pulses of electromagnetic radiation, wherein an envelope of said pulses is modulated, e.g. with respect to amplitude and/or frequency, according to the detected sound. Thereby, acoustic waves generated by the pulses in the ear resemble the detected sound. This is described in more detail in conjunction with FIG. 4 below.

In present example, the irradiation source 4 comprises both a laser source 4a, e.g. a laser diode, and a radiation guiding element 4b, e.g. an optical fiber, which is coupled to the laser source 4a and configured to guide the pulses of electromagnetic radiation from the laser source 4a to the medium 2. Preferably, the radiation guiding element 4b is flexible such that a distal end thereof may be arranged in the ear 20 and/or optically coupled to the medium 2, while the laser source 4a, which is optically coupled to a proximal end of the radiation guiding element 4b, may be kept or stored in a separate and/or remote location away from the medium 2, e.g. behind the ear 20. Alternatively, the irradiation device 1 including irradiation unit 4 and control unit 5 is formed and/or dimensioned to be implanted in the ear 20.

Alternatively, the irradiation source 4 may comprise, instead of a laser source 4a, a light-emitting device (LED) having a sufficient power and preferably a broader bandwidth than a laser source 4a.

FIGS. 3a) and 3b) show examples of a time course of power P or intensity I of a pulse of electromagnetic radiation in the top part, and a corresponding optoacoustic response, indicated as pressure p versus time t, in the bottom part.

The pulses shown by a solid line in the top part of FIGS. 3a) and 3b) are shaped, e.g. by an according control of the radiation source 4 by a control unit 5 (see FIGS. 1 and 2), such that an absorption of the pulse energy in a radiation absorbing medium generates only a single acoustic wave, also referred to as a pressure pulse, in the medium. This is achieved by a steep increase, see FIG. 3a), or decrease, see FIG. 3b), of the power P or intensity I of the pulses over a short period of time at the rising edge or falling edge, respectively, of the pulse, whereas a subsequent decrease or preceding increase, respectively, in power P or intensity I of each pulse spans over an extended period of time.

Accordingly, the pulse shown in FIG. 3a) exhibits a, in particular steeply, rising edge 8a and a, in particular moderately or continuously, falling slope 9a, while the pulse shown in FIG. 3b) exhibits a, in particular moderately or continuously, rising slope 9b and a, in particular steeply, falling edge 8b.

In the example given in FIG. 3a), the optoacoustic response is caused by an expansion of a part of the radiation absorbing medium, associated with an increasing absorption of electromagnetic energy due to a steep rise in power P or intensity I at the rising edge 8a. Accordingly, the amplitude of the resulting so-called condensation sound pressure pulse (see solid line in bottom part of FIG. 3a) is positive. In contrast to the steeply rising edge 8a, the moderately or continuously falling slope 9a causes an accordingly moderately or continuously decreasing absorption of electromagnetic energy in the medium so that, via an according local contraction of the medium, no pressure pulse or only a pressure pulse with negligible amplitude is generated during the decrease.

In the example given in FIG. 3b), on the other hand, the optoacoustic response is caused by a contraction of the part of the radiation absorbing medium, associated with a decreasing absorption of electromagnetic energy due to a steep decrease in power P or intensity I at the falling edge 8b. Accordingly, the amplitude of the resulting so-called rarefaction sound pressure pulse (see bottom part of FIG. 3b) is negative. In contrast to the steeply falling edge 8b, the moderately or continuously rising slope 9b causes an accordingly moderately or continuously increasing absorption of electromagnetic energy in the medium so that, via an according local expansion of the medium, no pressure pulse or only a pressure pulse with negligible amplitude is generated during the increase.

By providing a series of accordingly shaped pulses of electromagnetic radiation, a series of either condensation or rarefaction sound pressure pulses is generated, which allows for an improved conversion of ambient sound into according optoacoustic sound pressure pulses in a hearing aid device, like the one shown in FIG. 2.

For comparison, the dashed line in the top part of FIG. 3a) shows an example of the time course of power P or intensity I of a conventional rectangular pulse exhibiting both a steeply rising edge 8a and a steeply decreasing edge 8a'. The corresponding optoacoustic response (see bottom part of FIG. 3a) exhibits both a condensation sound pressure pulse having a positive amplitude (solid line) and a rarefaction sound pressure pulse having a negative amplitude (dashed line).

FIG. 3c) shows an example of a time course of power P or intensity I of a pulse of electromagnetic radiation exhibiting both an accordingly moderate or continuous increase of the rising slope 9c and an accordingly moderate or continuous decrease of the falling slope 9d. Like with the above examples of pulses exhibiting a falling slope 9a and a rising slope 9b given in FIGS. 3a) and 3b), the moderately or continuously rising and falling slope 9c and 9d cause an accordingly moderately or continuously increasing or decreasing, respectively, absorption of electromagnetic energy in the medium so that, by an accordingly weak local expansion or contraction, respectively, of the medium, no pressure pulses or only pressure pulses with negligible amplitude are generated.

In this way, the occurrence of undesired optoacoustic waves in response to an application of pulses of electromagnetic radiation to a medium can be efficiently avoided or at least significantly reduced, which is of particular advantage in general laser surgery and laser ear surgery.

FIG. 3d) shows another example of a time course of power P or intensity I of a pulse of electromagnetic radiation, which is particularly advantageous in laser surgery applications. Similarly to the example shown in FIG. 3c), the time course exhibits both a moderate or continuous increase of the rising slope 9c and an accordingly moderate or continuous decrease of the falling slope 9d. In present example, however, the laser pulse is a long pulse which exhibits a long plateau between the rising slope 9c and falling slope 9d. In this way, particularly high energy amounts can be deposited in the medium 2, while no pressure pulses or only pressure pulses with negligible amplitude are generated in response to the rising and falling slopes 9c, 9d. In this respect, the above elucidations in conjunction with FIG. 3c) apply accordingly. Preferably, the overall duration of the laser pulse, including the durations of the rising and falling slope and the plateau, corresponds to at least 5, 10, 20 or 0 times the duration of the rising slope and/or falling slope.

In the examples given in FIGS. 3a) to 3d), the time course of the power P or intensity I of the moderately or continuously falling slope 9a, 9d or rising slope 9b, 9c of the pulses follows a curved line, e.g. an exponential decay or increase. However, the occurrence of an optoacoustic response during the fall or rise of the pulse can also be avoided or at least significantly reduced by other shapes, e.g. a linear decrease or increase, respectively, sawtooth-shaped pulses etc.

Generally speaking, an occurrence of an optoacoustic response during the fall or rise of a pulse of electromagnetic radiation is avoided or at least significantly reduced, if the gradient (Δpower/Δt or Δintensity/Δt) of the falling or rising slope is limited, i.e. below a predetermined gradient. Preferably, a maximum gradient of the falling slope 9a, 9d and/or the rising slope 9b, 9c is smaller than a predetermined gradient value, which is preferably chosen such that the change in deposition rate of electromagnetic energy attributed to the rising or falling slope 9a, 9d or 9b, 9c in the radiation absorbing medium is below a threshold. Preferably, said threshold indicates or corresponds to the onset of the generation of acoustic waves having an amplitude which is strong enough to stimulate inner or outer hair cells and/or spiral (cochlear) ganglion neurons (SGNs) in a human ear.

Accordingly, a gradient of the rising edge 8a and/or the falling edge 8b, which may be continuously or discontinuously rising or falling edges, is preferably larger than the predetermined gradient value, in particular such that the change in deposition rate of electromagnetic energy in the radiation absorbing medium attributed to the rising or falling edge 8a, 8b is above the threshold.

In particular, the maximum gradient of the gradual increase or decrease of the power P or intensity I of the pulse, given by $$\frac{\Delta P}{\Delta t} \text{ or } \frac{\Delta I}{\Delta t},$$

is chosen to be less than a predetermined gradient value given by the maximum power $P_{max}$ or maximum intensity $I_{max}$ of the pulse and the thermal confinement time constant $\pi_t$, characterizing the time after which half of the (thermal) energy deposited in a part of the radiation absorbing medium has dissipated, e.g. into surrounding tissue, fluid or a, preferably specifically designed, absorber belonging to the device. The thermal confinement time constant $$\tau_t = \frac{d^2}{4\alpha_{th}}$$

is given by the absorbing volume, where d is the characteristic length of heat heterogeneity, e.g. the dimension of the optically absorbing target or the decay constant of the, in particular optical, energy deposition, and $\alpha_{th}$ is the thermal diffusivity.

For example, the maximum power limit common in surgical laser applications for ear surgeries is approx. $P_{max}$=10 W. Assuming a fiber core or laser beam diameter of 50 μm and water ($\alpha_{th}$=0.143 10-6 m²/s) as an absorber at a wavelength of sufficient high absorption leads to $\pi_t$=4.4 ms. This in turn limits the maximum gradient of the rising and/or falling slope 9a, 9b of the laser pulse to less than $$\frac{\Delta P_{max}}{\Delta \tau_t} = 2300 \frac{W}{s}$$

to suppress me optoacoustic response sufficiently. Reduction of the characteristic length to d=1 μm at the same power and conditions results in $\pi_t$=1.7 μs and a limitation for the gradient to less than $$\frac{\Delta P_{max}}{\Delta \tau_t} = 5.7 \cdot 10^6 \frac{W}{s}.$$

Alternatively, the maximum gradient of the pulse may be chosen to be less than a predetermined gradient value given by the maximum power $P_{max}$ or intensity $I_{max}$ of the pulse and the stress confinement time constant $\tau_p$, characterizing the time after which half of the (thermally induced) stress caused by expansion or contraction of a part of the radiation absorbing medium has dissipated, e.g. into surrounding tissue. Because stress dissipates faster than thermal energy, in this embodiment the predetermined gradient value is higher than in the embodiment mentioned above.

For example, the duration of the successive or gradual increase or decrease of the power P or intensity I of a pulse is at least 5%, in particular at least 10%, of the overall duration of the pulse. For example, a laser pulse with an overall duration of 100 μs exhibits a continuous increase from zero to maximum power or intensity and/or a continuous decrease from maximum to zero power or intensity during at least 5 μs, preferably during at least 10 μs. In this way, it is ensured that the rising or falling slope is not too steep so that a generation of according optoacoustic sound pressure waves is reliably avoided.

In some embodiments, for example in laser surgery applications, in which particularly long pulses, e.g. with a pulse duration of at least 10 ms, in particular at least 100 ms, are deployed, the duration of the increase or decrease of the power P or intensity I of the pulse may be shorter or even considerably shorter than 10%, in particular shorter than 5%, preferably shorter than 2.5% the overall duration of the pulse.

Alternatively or additionally, the duration of the successive or gradual increase or decrease of the power or intensity of a pulse is at most 30%, in particular at most 20%, of the overall duration of the pulse. For example, a laser pulse with an overall duration of 100 μs exhibits a continuous increase from zero to maximum power or intensity and/or a continuous decrease from maximum to zero power or intensity during at most 30 μs, preferably during at most 20 μs. In this way, it can be ensured that the total laser energy of the pulse is not too much or not considerably reduced by the continuously rising and/or falling slope of the pulse, although a generation of unwanted optoacoustic noise is avoided or reduced significantly.

Figure 3:
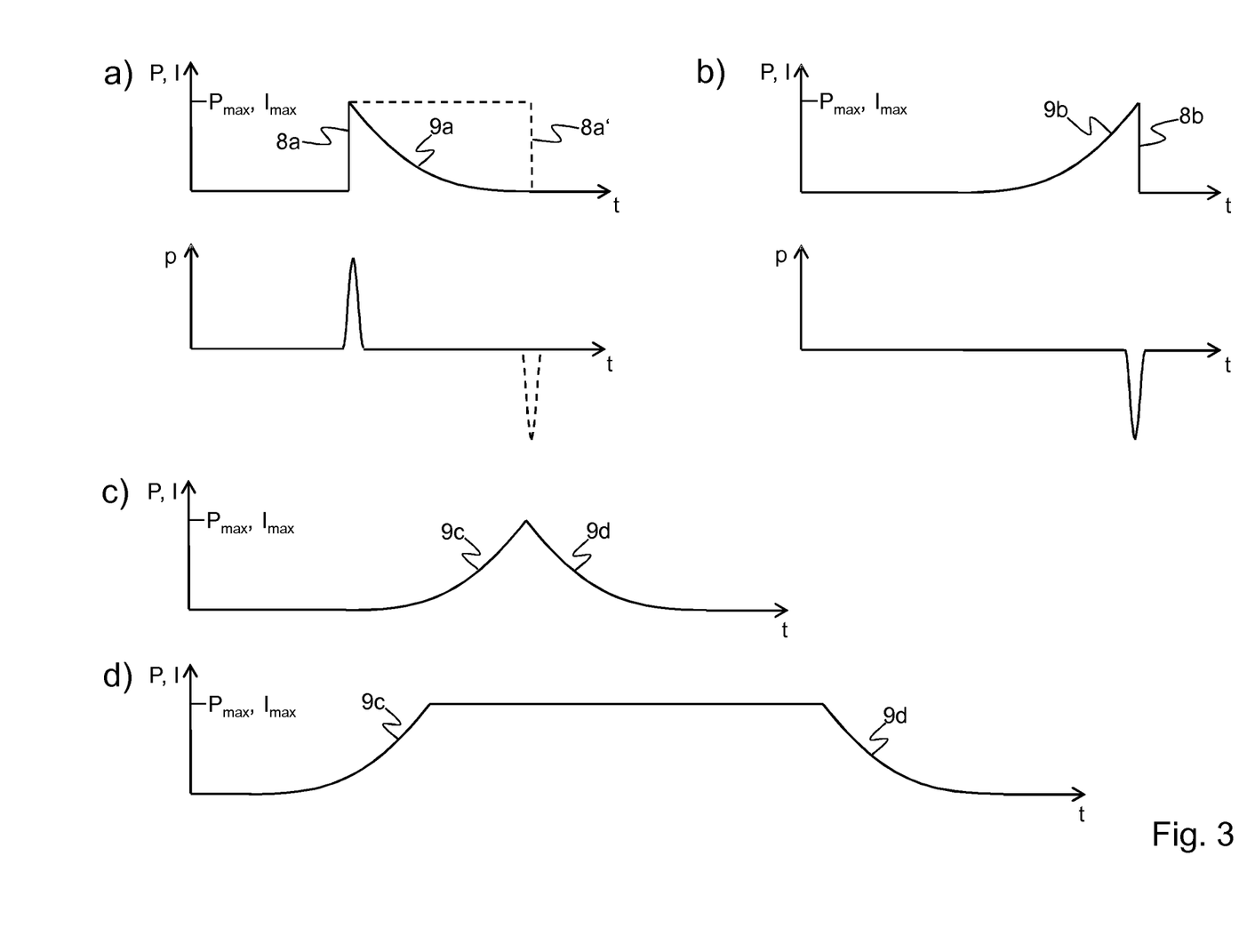
FIG. 3 shows examples of a time course of power or intensity of a pulse of electromagnetic radiation (3a to 3d) and a respective optoacoustic response (3a and 3b only)
Figure 4:
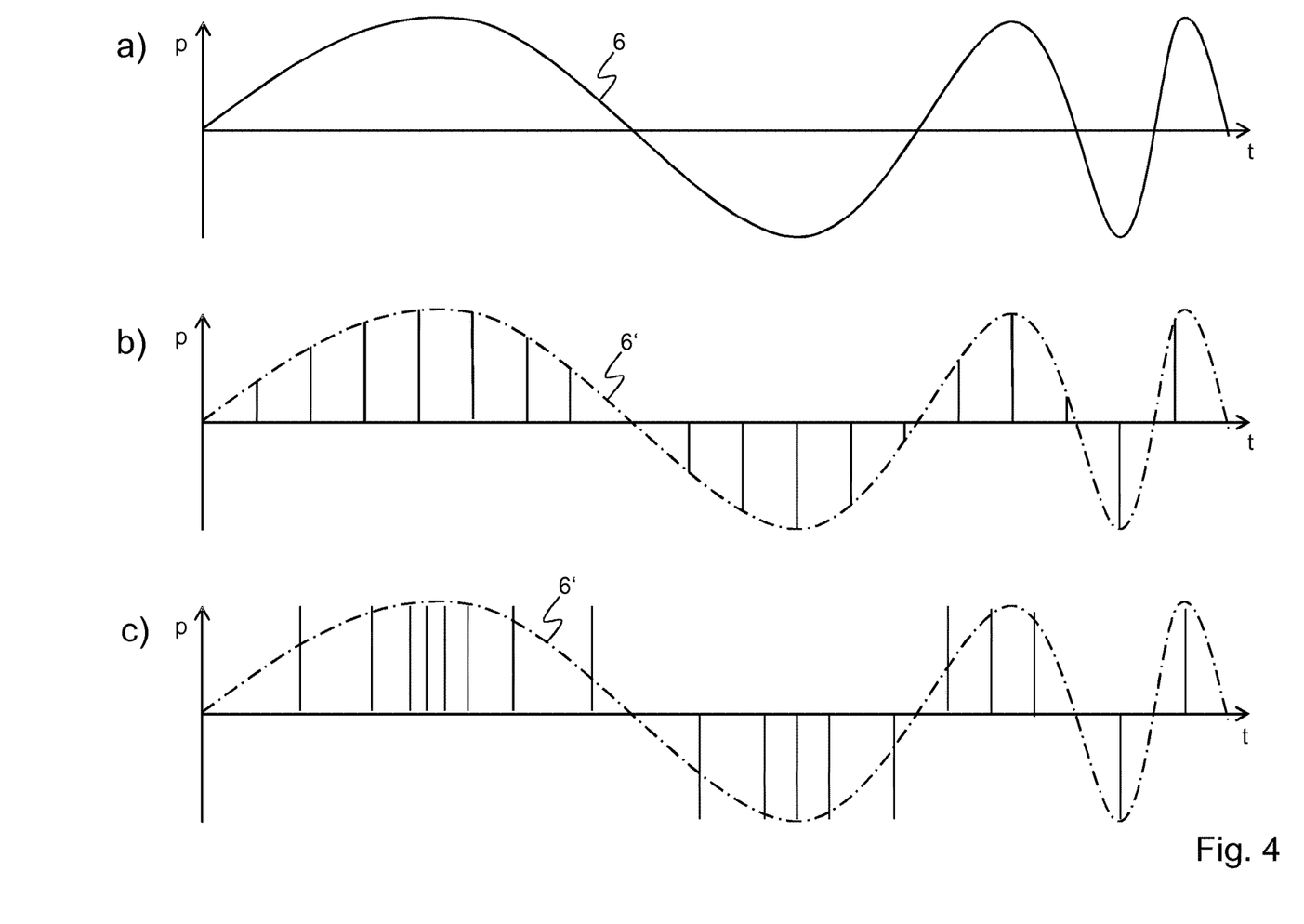
FIG. 4 shows examples of amplitude and frequency modulation.

FIG. 4 shows an example of an acoustic wave 6 generated in a radiation absorbing medium in response to a series of amplitude and/or frequency modulated pulses of electromagnetic radiation, exhibiting a rising slope or a falling slope as explained in conjunction with FIG. 3 above. The perceived sound is a result of a subsequent (inherent) low-pass filtering of the ear, wherein frequency components of the acoustic wave 6 up to a threshold frequency are passed and perceived, whereas frequency components exceeding the threshold frequency are filtered out and not perceived.

FIG. 4a) shows a time course of a pressure amplitude p of an acoustic wave 6, characteristic of a sound propagating in a radiation absorbing medium, e.g. a biphasic stimuli for stimulation of a component of an ear. In order to reproduce said sound wave optoacoustically, a series of modulated pulses of electromagnetic radiation may be irradiated onto the radiation absorbing medium.

In order to capture the time course of the amplitude of the acoustic wave 6, the amplitude, i.e. the maximum power or maximum intensity, of each pulse of a series of equidistant pulses of electromagnetic radiation is modulated (amplitude modulation). In this way, optoacoustic responses which are characteristic for the modulation, i.e. pressure pulses with pressure amplitudes p corresponding to the amplitude of the pulses of electromagnetic radiation, are generated in the radiation absorbing medium as shown in FIG. 4b). By controlling the amplitude of each of the pulses of electromagnetic radiation accordingly, an envelope 6' of the resulting pressure pulses resembles the time course of the amplitude p of the acoustic wave 6 shown in FIG. 4a).

Alternatively or additionally, the frequency of the pulses of electromagnetic radiation, i.e. the temporal distance or time interval between successive pulses, may be modulated (frequency modulation) such that the temporal succession of the resulting pressure pulses corresponds to the acoustic wave 6 as shown in FIG. 4c). In particular, the integrated pressure p of the resulting pressure pulses corresponds to an envelope 6' of the pulses resembling the time course of the amplitude p of the sound wave 6.

The sign of the amplitude p of the pressure pulses, i.e. whether the amplitude p is positive or negative, may be determined by applying pulses of electromagnetic radiation with an according steeply rising edge (positive amplitude p) and moderately falling slope, or with an according moderately rising slope and steeply falling edge (negative amplitude p), as elaborated in conjunction with FIG. 3 above.

In these embodiments, the modulation frequency of the amplitude or frequency modulation of the pulses of electromagnetic radiation preferably lies above an upper cutoff frequency of the radiation absorbing medium, such that the resulting optoacoustic response, i.e. the pressure signals, in the radiation absorbing medium are low-pass filtered resulting in a pressure signal replicating the acoustic wave 6 with high fidelity.

What is claimed is:

1. An irradiation device for irradiating a radiation absorbing medium with electromagnetic radiation, the irradiation device comprising a radiation source configured to generate one or more pulses of electromagnetic radiation and to irradiate the medium with the one or more pulses of electromagnetic radiation,
    wherein a control unit is configured to control the radiation source such that a time course of a power or intensity of at least one pulse of the one or more pulses of electromagnetic radiation exhibits a rising slope and/or a falling slope, the rising slope and/or falling slope having a maximum gradient which is smaller than a predetermined gradient value, whereby a generation of optoacoustic waves in the medium in response to the rising slope or falling slope, respectively, is avoided or significantly reduced,
    wherein the predetermined gradient value is calculable by considering:
        a maximum power applied to the medium by irradiating the medium with the at least one pulse of electromagnetic radiation,
        a length characterizing a dimension of a heat heterogeneity in the medium and/or corresponding to a decay constant of an electromagnetic energy deposition in the medium, and
        a thermal diffusivity of the medium.

2. The irradiation device according to claim 1, wherein the rising slope and/or falling slope is a continuously or gradually rising slope or a continuously or gradually falling slope, respectively.

3. The irradiation device according to claim 1, wherein the falling slope is a linearly falling slope or the rising slope is a linearly rising slope.

4. The irradiation device according to claim 1, wherein the falling slope is differentiable or the rising slope is differentiable.

5. The irradiation device according to claim 1, wherein a maximum gradient of the rising slope or falling slope, respectively, corresponds to a maximum of an absolute value of a first time derivative of the falling slope or rising slope, respectively.

6. A hearing aid device for a human ear, the hearing aid device comprising:
    an irradiation device for irradiating a radiation absorbing medium with electromagnetic radiation, the irradiation device comprising a radiation source configured to generate one or more pulses of electromagnetic radiation and to irradiate the medium with the one or more pulses of electromagnetic radiation,
    wherein the radiation source or a part thereof is dimensioned and/or designed for being placed in an ear, in particular in a middle or inner ear, and designed for irradiating a component of the ear or a radiation absorbing medium located proximate to or adjacent to a component of the ear with the at least one pulse of electromagnetic radiation,
    wherein a control unit is configured to control the radiation source such that a time course of a power or intensity of at least one pulse of the one or more pulses of electromagnetic radiation exhibits either
    a falling slope and a rising edge, said falling slope having a maximal gradient which is smaller than a predetermined gradient value, or
    a rising slope and a falling edge, said rising slope having a maximal gradient which is smaller than a predetermined gradient value,
    whereby the least one pulse of the one or more pulses of electromagnetic radiation induces a single dominant optoacoustic wave in the component of the ear or the radiation absorbing medium in response to the rising edge or falling edge, respectively, whereas a generation of optoacoustic waves in response to the rising slope or falling slope, respectively, is avoided or significantly reduced,
    wherein the predetermined gradient value is calculable by considering: a maximum power applied to the medium by irradiating the medium with the at least one pulse of electromagnetic radiation, a length characterizing a dimension of a heat heterogeneity in the medium and/or corresponding to a decay constant of an electromagnetic energy deposition in the medium, and a thermal diffusivity of the medium.

7. The hearing aid device according to claim 6, wherein the rising edge is a discontinuously rising edge or the falling edge is a discontinuously falling edge.

8. The hearing aid device according to claim 6, wherein a maximum of the absolute value of a first time derivative of the rising edge and/or the maximum of the absolute value of a first time derivative of the falling edge is larger than the predetermined gradient value.

9. The hearing aid device according to claim 6, wherein the time course of the power or intensity of the at least one pulse exhibits a sawtooth shape.

10. The hearing aid device according to claim 6, wherein the radiation source comprises a radiation guiding element having a proximal end to which the at least one pulse of electromagnetic radiation is coupled, and a distal end and being configured to guide the at least one pulse of electromagnetic radiation from the proximal end to the distal end, wherein the distal end is dimensioned and/or designed for being placed in the ear, in particular in the middle or inner ear, and designed for emitting the at least one pulse of electromagnetic radiation to the component of the ear or to the radiation absorbing medium located proximate to or adjacent to a component of the ear.

11. A laser surgery device, in particular for laser ear surgery, the laser surgery device comprising:
- an irradiation device for irradiating a radiation absorbing medium with electromagnetic radiation, the irradiation device comprising a radiation source configured to generate one or more pulses of electromagnetic radiation and to irradiate the medium with the one or more pulses of electromagnetic radiation, wherein
- a control unit is configured to control the radiation source such that a time course of the power or intensity of at least one pulse of the one or more pulses of electromagnetic radiation exhibits a rising slope and/or a falling slope, the rising slope and/or falling slope having a maximum gradient which is smaller than a predetermined gradient value, whereby a generation of optoacoustic waves in the medium in response to the rising slope or falling slope, respectively, is avoided or significantly reduced, wherein the predetermined gradient value is calculable by considering:
  - a maximum power applied to the medium by irradiating the medium with the at least one pulse of electromagnetic radiation;
  - a length characterizing a dimension of a heat heterogeneity in the medium and/or corresponding to a decay constant of an electromagnetic energy deposition in the medium; and
  - a thermal diffusivity of the medium;
- wherein the radiation source comprises a laser source and is dimensioned and/or designed for irradiating an organ of a human, in particular a component of an ear, with the at least one pulse of electromagnetic radiation.

12. The laser surgery device according to claim 11, wherein the control unit is configured to control the radiation source such that the time course of the power or intensity of the at least one pulse exhibits both a rising slope having a maximal gradient which is smaller than a predetermined gradient value and a falling slope having a maximal gradient which is smaller than a predetermined gradient value.

13. A method for irradiating a radiation absorbing medium with electromagnetic radiation, the method comprising:
- generating one or more pulses of electromagnetic radiation and irradiating the medium with the one or more pulses of electromagnetic radiation, wherein
- a time course of a power or intensity of at least one pulse of the one or more pulses of electromagnetic radiation exhibits a rising slope and/or a falling slope, the rising slope and/or falling slope having a maximum gradient which is smaller than a predetermined gradient value, whereby a generation of optoacoustic waves in the medium in response to the rising slope or falling slope, respectively, is avoided or significantly reduced, wherein the predetermined gradient value is calculable by considering:
  - a maximum power applied to the medium by irradiating the medium with the at least one pulse of electromagnetic radiation;
  - a length characterizing a dimension of a heat heterogeneity in the medium and/or corresponding to a decay constant of an electromagnetic energy deposition in the medium; and
  - a thermal diffusivity of the medium.

* * * * *